United States Patent [19]

Donnelly et al.

[11] Patent Number: 5,041,286
[45] Date of Patent: Aug. 20, 1991

[54] PROCESS FOR RECONFIGURING KERATIN FIBRE

[75] Inventors: Roberta A. Donnelly; Patrick J. Donnelly, both of Belrose, Australia

[73] Assignee: Yasmin Products Pty. Limited, Alexandria, Australia

[21] Appl. No.: 385,283

[22] Filed: Jul. 25, 1989

[30] Foreign Application Priority Data

Jul. 26, 1988 [AU] Australia ................. PI9481

[51] Int. Cl.$^5$ ............. A61K 7/09; A45D 7/04
[52] U.S. Cl. ................... 424/71; 424/72; 132/205; 132/209
[58] Field of Search ............ 424/71, 72; 132/205, 132/209

[56] References Cited

U.S. PATENT DOCUMENTS

| | | |
|---|---|---|
| 2,564,722 | 8/1951 | Reed .................. 132/204 |
| 2,631,965 | 3/1953 | Schnell ............... 424/72 |
| 2,736,323 | 2/1956 | McDonough ........ 132/206 |
| 3,024,218 | 3/1962 | Stevens .............. 521/21 |
| 3,025,218 | 3/1962 | Strain ................ 424/72 |
| 3,148,126 | 9/1964 | Martin ............... 132/203 |
| 3,736,944 | 6/1973 | Ghilardi ............. 132/204 |
| 3,842,848 | 10/1974 | Karjala ............. 132/204 |
| 4,044,782 | 8/1977 | Adrion .............. 132/207 |
| 4,134,411 | 1/1979 | Yamazaki ........... 132/205 |
| 4,192,863 | 3/1980 | Kondo ............... 424/72 |
| 4,313,933 | 2/1982 | Yamazaki ........... 424/72 |
| 4,366,827 | 1/1983 | Madrange .......... 132/204 |
| 4,409,204 | 10/1983 | Lang ................. 424/70 |
| 4,494,557 | 1/1985 | Nagel ................ 132/204 |
| 4,547,365 | 10/1985 | Kubo ................. 424/71 |
| 4,548,811 | 10/1985 | Kubo ................. 424/71 |
| 4,659,566 | 4/1987 | Petrow .............. 424/71 |

FOREIGN PATENT DOCUMENTS

| | | |
|---|---|---|
| 7539887 | 1/1988 | Australia . |
| 2066310 | 7/1981 | United Kingdom . |
| 2078804 | 1/1982 | United Kingdom . |

Primary Examiner—Thurman K. Page
Assistant Examiner—Susan S. Rucker
Attorney, Agent, or Firm—Ladas & Parry

[57] ABSTRACT

A process of recofiguring keratin fibre is disclosed. The process includes rolling, winding, curling, looping lapping, folding, twirling, bending, curving, twisting, coiling, twining, entwining or straightening the keratin fibre or leaving the keratin fibre unchanged. A reducing agent is then applied to the keratin fibre to reduce cystine disulfide linkages and other susceptible linkages in the keratin fibre. An oxidizing agent is applied to the keratin fibre having the reducing agent, to set cystine disulfide linkages in the keratin fibre. The reducing agent and the oxidizing agent are then removed from the keratin fibre by rinsing the keratin fibre.

15 Claims, No Drawings

PROCESS FOR RECONFIGURING KERATIN FIBRE

TECHNICAL FIELD

This invention relates to a process of reconfiguring keratin fibre.

BACKGROUND ART

Keratin fibre is commonly reconfigured by humans when they have their hair permanently waved. However, permanent waving of human hair is not the only application of permanent waving. For example, the textile industry has a need to permanently wave wool for some applications.

The conventional permanent waving process for human hair is performed in the following manner:

(i) Human hair is cleaned by washing with shampoo, for example, and then rinsed.

(ii) The hair is then typically wound onto a mandrel.

(iii) A reducing agent is applied to the hair to reconfigure the hair. The reducing agent is left on the hair for a sufficient time period to ensure reconfiguration of the hair. This time period depends upon the concentration of reducing agent, pH of solution, and texture and quality of the hair. Generally, for the process of permanently waving human hair the reducing agent is typically left on the hair for a time period which can be between 5 and 45 minutes. Human hair is considered reconfigured, from a chemical point of view, when the S—S cystine linkages of the hair and possibly other bonds within the hair have been weakened or broken.

(iv) The reducing agent is then thoroughly rinsed from the hair. The rinsing period depends upon the length and type of hair, concentration of reducing agent and complexity and quantity of mandrels employed. For the permanent waving of human hair the rinsing period is typically from 10 to 30 minutes. During the rinsing of their hair a person is typically seated at a basin and copious amounts of water are used to flush the reducing agent from the hair.

(v) The hair is then blotted to remove any excess moisture.

(vi) An oxidizing agent is then applied to the hair and left there for sufficient time to set the cystine linkages. The length of the period for which the oxidizing agent is left on the hair depends on the concentration of the oxidizing agent and the type of oxidizing agent employed. The oxidizing agent reconstitutes or sets the cystine S—S linkages in the hair to the configuration of the hair around the mandrel.

(vii) The hair is then rinsed to remove the oxidizing agent.

There are many cold and warm wave products which are utilized in present permanent waving processes. As far as the present inventors are aware the hairdressing industry, which is the principle user of products used in the current permanent waving process for keratin fibre, specifically human hair, universally has available to it products which all require and specify rinsing of the hair with water between the application of the reducing agent and the application of the oxidizing agent.

The conventional process for permanent waving of hair requires two rinsing steps:

(a) a mid process rinsing step when hair is most vulnerable to damage, that is, after the reducing agent has swollen the hair and dishevelled the cystine. This rinsing step takes place prior to the application of an oxidizing agent used to reset the linkages and bonds; and (b) a final rinsing step after the application of oxidizing agent to set the linkages. A major disadvantage of present processes for reconfiguring keratin fibre and more particularly processes for permanent waving of human hair is associated with the lengthy rinsing of the reducing agent from the hair before application of an oxidizing agent. This rinsing takes place whilst the cystine S—S linkages, and other linkages, in the hair are in an unstable or reactive state. The structure of the hair can be degraded when movement occurs whilst the hair is in this reactive state. Further, rinsing human hair is a time consuming and uncomfortable process for both the person carrying out the process and the person on which the process is being done. The person on which the process is being performed is subjected to a continuous, uncomfortable rinsing period of up to 30 minutes prior to the application of the oxidizing agent. Typically the person has his or her neck bent back over a rinsing tray and this can result in a stiff and/or sore neck. Also reducing agent and/or water can be splashed over such a person during this rinsing step. A major economical disadvantage relating to the rinsing of reducing agent from the hair is the time it adds to the permanent waving process of up to 30 minutes. This reduces the number of clients on which an operator can carry out the permanent waving process.

OBJECT OF INVENTION

It is an object of this invention to provide a process of reconfiguring keratin fibre which does not include a rinsing step after the application of reducing agent and before the application of oxidizing agent to the keratin fibre.

DISCLOSURE OF INVENTION

The inventors have developed a process of reconfiguring keratin fibre which does not include a rinsing step after the application of reducing agent and before the application of oxidizing agent to the keratin fibre.

According to a broad form of this invention there is provided a process of reconfiguring keratin fibre comprising:

rolling, winding, curling, looping, lapping, folding, twirling, bending, curving, twisting, coiling, twining, entwining, or straightening the keratin fibre or leaving the keratin fibre unchanged;

applying a reducing agent to the keratin fibre to reduce cystine disulfide linkages and other susceptible linkages in the keratin fibre;

applying an oxidizing agent to the keratin fibre having the reducing agent, to set the cystine disulfide linkages in the keratin fibre;

removing the reducing agent and the oxidizing agent from the keratin fibre by rinsing the keratin fibre.

The keratin fibre can be human hair, dog's hair, wool from sheep or goats or keratin fibre on or from other suitable sources.

Generally the process includes the step of washing the keratin fibre before the keratin fibre is rolled, wound, curled, looped, lapped, folded, twirled, bent, curved, twisted, coiled, twined, entwined or straightened or before the keratin fibre is reconfigured but otherwise left unchanged.

The reducing agent can be thioglycolic acid or its derivatives and/or other organic or inorganic reducing substances.

Further examples of reducing agents include:

α-Thioglycerol,
β-mercaptoethane sulfonic acid salts,
β-aminoethylmercaptan and mercaptoethyl alcohol,
isomeric mercaptobutane sulfonates,
β-mercaptopropionamide,
mercaptoethylacetamide,
thioglycolamide,
thiolactic acid,
methyl mercaptoethyl sulfone,
mercaptoethyl nitrile,
mercaptoethyl trifluoroacetamide,
thioparaconic acid and its derivatives,
α,α'-dimercaptoadipic acid,
N-acetyl cysteine and
1,4-dimercapto-2,3-butanediol.

Derivatives of Thioglycolic acid including:

carbaminyl thioglycolic acid,
glycolic acid esters of di- and trithiocarbonic acids,
dithiocarbamyl derivatives
heterocyclic compounds, such as 2,4-thiazoledione,
thioglycolamide,
esters and amides of thioglycolic acid,
monothiopropylene glycol,
α, thioglycerol,
various esters of monothioglycol,
thioglycolic acid hydrazide,
β-aminoethyl thioglycol amide,
thioglycolic acid amides of amino acids and
bis-thioglycolic acid imide.

Non-mercaptan reducing agents including:

organic and inorganic salts of sulfurous acid,
bisulfites of organic nitrogen,
guanidinium or ammonium bisulfite,
alkyl or aryl substituted guanidinium bisulfites,
formamidine sulfinic acid and its potassium salt,
potassium borohydride,
sodium borohydride and anhydrous sulfide and
phosphine derivatives, such as tetrakishhydroxymethyl-
  phosphonium chloride.

The reducing agent is typically in dissolved in an aqueous solution at a concentration of from 5 to 15% by weight. The aqueous solution of reducing agent can include other additives such as sequestrene disodium EDTA, ammonium hydroxide, and carbonic acid.

The reducing agent is typically left on the keratin fibre for a period of from 5 to 40 minutes before application of the oxidizing agent.

The oxidizing agent can be sodium bromate, hydrogen peroxide, organic peroxides, e.g. urea peroxide or inorganic metallic peroxides, e.g. sodium perxiode or sodium chlorate in 3%–15% by wt. aqueous media.

Further specific examples of oxidising agents include:
Chemical oxidising agents including:

hydrogen peroxide,
potassium bromate,
sodium perborate,
sodium bromate,
sodium perborate monohydrate,
sodium chlorite,
urea peroxide,
melamine perhydrate and
perhydrates of α-aminoalkylphosphonic acids.

Non-oxidising chemical "neutralising" agents including:

S-oxides of N-dialkyl-substituted thioalkanoic acid amides,
S-oxides of sulfinamides and
alkaline polythionates.

Air can also be used as an oxidising agent.

The oxidizing agent is typically dissolved in an aqueous solution at a concentration of from 3 to 15% by weight. The aqueous solution of reducing agent can include other additives such as mixed cationic cellulosic polymers, opacifier, colour, perfume added as preferred and Vitron (trade mark of Yasmin Products Pty Ltd).

The chemical composition of Vitron is:

| | |
|---|---|
| Alcohol | 32% |
| Vinylpyrrolidone/vinyl acetate copolymer | 6% |
| Quaternized copolymers of Vinylpyrrolidone and K-Dimethylaminoethyl methacrylate | 12% |
| Amino Acids | 3% |
| Water | 47% |
| Perfume, colour q.s. | |

The oxidizing agent is typically left on the keratin fibre for a period of from 5 to 30 minutes before rinsing.

The reducing agent:oxidizing agent ratio is generally from 1:0.3 to 1.5:1 w/w. A reducing agent:oxidizing agent ratio of 1.2:1 provides excellent results when 12% w/w thioglycolic acid is used as the reducing agent and 10% w/w sodium bromate is used as the oxidizing agent.

The relationship of the reducing agent to the oxidizing agent is such that only a minimum amount of oxidizing agent is required for neutralization of the reduction agent. However, a considerable excess is desirable and required to promote a successful reaction within the acceptable time span and for the in situ process.

A typical process, according to the invention, of permanently waving human hair is as follows:

(a) Cleanse hair so that it is free of dirt, oil and other substances which can impair the penetration of solutions. Towel dry.

(b) Prior to winding the hair onto suitable mandrel, the hair can be treated with a solution of variable compositions which are employed to "even out" the porosity and/or protect those parts of the hair which do not want to be affected by the reducing medium to the same degree as other parts of the hair. This solution can contain amino acids of various molecular weight, quaternary ammonium compounds, medium to high molecular weight quaternized copolymers and other suitable "protecting" chemicals in an aqueous or alcoholic solution.

(c) Roll or wind hair sections onto mandrels of desired size and shape to determine the reconfiguration of the hair and secure.

(d) Apply REDUCING MEDIUM which can be composed of thioglycolic acid or its derivatives and/or other organic or inorganic reducing substances compatible with human skin capable of reducing the cystine linkages in the keratin in alkaline, acid or neutral aqueous media, at all temperatures compatible with human skin.

This solution must be capable of penetration into the hair so that the S—S linkages can be softened.

In the instance of an alkaline solution the thiols will function. However, in acid or neutral solutions other reducing agents can perform better.

The concentrate of the reducing agent should be between 5%–15% depending upon strength required for different types of keratin fibres. Sequestring agents, opacifiers, colours and perfumes can be included to enhance appearance of the finished product. The length of time required to process will vary, depending on strength of solution, type and volume of hair, from 5 to 40 minutes.

(e) When the desired reconfiguration has been achieved, DO NOT RINSE the reducing medium from the hair.

(f) The permanent reconfiguration of the hair is "set" by the application of an aqueous solution of a suitable oxidising agent. Generally these take the form of sodium bromate, hydrogen peroxide, organic peroxides, e.g. urea peroxide or inorganic metallic peroxides, e.g. sodium peroxide or sodium chlorate in aqueous media—3%–15% depending on chemical used and in relation to the reducing agent previously employed.

The length of time required to oxidise will vary, depending upon agent employed, concentration and type of reducing agent, type and volume of hair, from 5 to 20 minutes. The application of the neutraliser (oxidising agent) can be in one or two steps, utilizing a volume equivalent to that employed in the reduction medium. The mandrels are removed either between the neutralizing steps or after process is completed.

(g) An acid conditioning rinse is applied to the hair either before or after rinsing the reaction products from the hair. If applied after rinsing, a further rinse is required. Advantages of the invention include:

A. Greater comfort is afforded to the client. There is not the long period of time at the basin with one's head leaned backwards for up to one half an hour.

B. The hair is more completely neutralized (oxidised) as the oxidising agent has better access to the linkages within the hair which have been softened by the reducing agent.

C. The hair is less likely to suffer damage which occurs during the rinsing and blotting stages of conventional processes. Conventionally, the rinsing and blotting occur whilst the hair structure is in a fragile, disorientated state, when the S—S linkages are softened. Should these be disturbed before the re-setting of the bond occurs the rinsing elutes vital substances which are lost in the process and are irreplaceable.

D. The professional operator is required to spend far less "hands-on" time with our invention. This time, up to 20–30 minutes can be applied to other income-producing work in the salon.

E. Far less hot water is utilized for each perming procedure. Approximately 30 liters of hot water less is used. Multiplied by a number of perms per week, this is an appreciable cost saving.

F. Far fewer towels are utilized for each perming procedure. Approximately 3 towels fewer are used. Multiplied by a number of perms per week, this is an appreciable cost saving.

G. Additional chemical treatments such as permanent dyeing, temporary dyeing, bleaching, streaking, highlighting, conditioning, etc., can be performed immediately after completion of the perming procedure. As complete neutralization has taken place, there is no need to wait two weeks, as often the recommendation of other manufacturers.

H. The manufactured cost of our product is comparable to other products of its type, so there is no price disadvantage.

BEST MODE AND OTHER MODES OF CARRYING OUT THE INVENTION

Preferred Process

A preferred process of permanently waving human hair is as follows:

1. Cleanse hair so that it is free of dirt, oil and other substances which can impair the penetration of solutions. Towel dry.

2. Prior to winding the hair onto suitable mandrels, treat the hair with an aqueous/alcoholic solution containing 1 part Vinylpyrrolidone/vinyl acetate copolymers to 2 parts Quaternized copolymers of Vinylpyrrolidone and Dimethylaminoethyl methacrylate, together forming 18% of the total solution, with the addition of 3% amino acids. Quantity to be applied is between 10–20 mls, depending upon length and volume of hair. Application should be particularly to the more porous parts of the hair.

This solution will "even out" the porosity and aid in protecting bonds which should not be affected by the reducing agent.

3. Roll or wind hair sections onto mandrels of desired size and shape to determine the reconfiguration of the hair and either leave the mandrel in place, or remove and secure the curled tress with a clip.

4. Apply REDUCING MEDIUM with the preferred composition of:

| | | |
|---|---|---|
| a. | Thioglycolic acid | 12% w/w |
| b. | Sequestrine Disodium EDTA | .0016% w/w |
| c. | Ammonium Hydroxide (30%) | 16% w/w |
| d. | Carbonic Acid | .8%–2.8% w/w |

The variation in Carbonic Acid produces a finished product with a pH range from 7.5 (for easier to wave hair) to 9.5 (for more difficult to wave hair).

e. Colouring, appropriate opacifier and perfume are added for consumer preference.

The above mixture is reacted in a non-metallic container from which air is excluded.

The length of time required to process the reduction product will vary, depending on which variety (pH) solution is employed, type and volume of hair, and desired result of the operation, from 5 to 40 minutes.

5. When the desired reconfiguration has been achieved, DO NOT RINSE the reducing medium from the hair.

6. Apply the oxidising (neutralising) agent in two steps, each of 5 minutes duration. Do not remove mandrels or clips between applications. Utilize a volume of oxidising medium equivalent to that employed of reduction medium. The preferred composition of the oxidising medium is:

| | | |
|---|---|---|
| a. | Sodium Bromate | 10% w/w |
| b. | Mixed Cationic Cellulosic Polymers | .5% w/w |
| c. | Opacifier, colour, perfume added q.s. | as preferenced. |
| d. | Vitron | 1% w/w |

7. When oxidising step is complete, remove mandrels and/or clips. Apply a quantity to suit of an acid conditioning rinse, and distribute throughout hair. Rinse hair.

The ratio of reduction agent to oxidation agent is 1.2:1 provides an excellent end result.

8. The hair can be immediately chemically treated, if desired, by permanent dyeing, temporary dyeing, highlighting, bleaching, streaking and/or conditioning.

The lack of a rinsing step after the application of reducing agent in the process of the invention when applied to the perming of human hair is readily apparent on comparing the conventional perming procedure of Comparative Example 1 with the perming procedure of the invention both of which set out in Example 1 below:

COMPARATIVE EXAMPLE 1

Conventional Perming Procedure

| | |
|---|---|
| SHAMPOO | The customer is shampooed at a basin to remove any dirt, oil or other impurities. The hair is then towel dried. |
| POROSITY EQUALIZER | The customer is taken to another chair, workstation, where a "porosity equalizer", or protein containing solution is sometimes applied. This is not always a requirement of manufacturers, but in practice often is done. |
| WINDING | The hair is sectioned and wound on mandrels of whatever shape or size deemed right for the type of curl required. Sometimes the hair is pre-dampened with a small amount of waving solution prior to winding. |
| SOLUTION APPLICATION | When winding is complete, sufficient solution is applied to saturate the hair, without excessive run-off. The volume required will vary depending on type and volume of hair. It is important that the hair not be wound too tightly so as to preclude sufficient absorption of waving solution. |
| PROCESSING TIME | The reducing solution is processed for a period of time which will vary from head to head and from time to time on the same head of hair. This period of time can be from 5 to 40 minutes, variable also by the particular solution utilized |
| RINSING | When the desired curl is achieved, the operator will have the customer taken back to the basin for the rinsing period. From the time the operator makes this decision to the time the rinsing actually commences, several minutes can pass, during which time processing continues. The actual rinsing with warm water will continue the processing action for a further period of time. The actual length of rinsing time will vary depending on type and quantity of mandrels used, as well as the efficiency, or lack of, of the person employed to do the rinsing, very often a junior employee. THIS PERIOD OF TIME CAN ENCOMPASS 15 TO 35 MINUTES. |
| BLOTTING | After the rinsing is completed, the hair is blotted with a towel to remove any excess moisture. Each roller is supposed to be evenly blotted. some remain unblotted there can be excess water remaining in the hair, thus diluting the oxidising agent which follows. The customer remains at the basin during this procedure, with her head leaned backwards over the basin. |
| NEUTRALIZER APPLICATION | The first amount of neutralizer (oxidising agent) is applied while the hair is still wound on mandrels. This solution remains for 2 to 10 minutes, depending on manufacturer. The mandrels are removed from the hair and the remaining portion of neutralizer is applied. It is the common practice in hairdressing salons to re-use neutralizer from the drip-tray. This second application remains for 2 to 10 minutes, depending on manufacturer. |
| RINSING/ CONDITIONING | The hair is then rinsed well, and an acid conditioner is often applied. This is massaged through the hair and then rinsed. |
| STYLING | Drying and styling of hair is performed, with caution used when blowaving. It is recommended to the customer that she not wash or blowave her hair for 2 to 3 days after a permanent wave as the air continues the oxidation process. |

EXAMPLE 1

Perming Process According to the Present Invention

| | |
|---|---|
| SHAMPOO | The customer is shampooed at a basin to remove any dirt, oil or other impurities. The hair is then towel dried. |
| POROSITY EQUALIZER | The customer is taken to another chair, workstation, where the hair has applied a solution which equalizes the porosity, and protects certain parts of the hair which do not want to be overprocessed. |
| WINDING | The hair is sectioned and wound on mandrels of whatever shape or size deemed right for the type of curl required. |
| SOLUTION APPLICATION | When winding is complete, sufficient solution is applied to saturate the hair, without excessive run-off. The volume required will vary depending on type and volume of hair. It is important that the hair not be wound too tightly so as to preclude sufficient absorption of waving solution. |
| PROCESSING TIME | The reducing solution is processed for a period of time which will vary from head to head and from time to time on the same head of hair. This period of time can be from 5 to up to 30 minutes, variable also by the particular solution utilized. |
| RINSING BLOTTING | A rinsing step is not performed at this stage. A blotting step is not performed at this stage. |
| NEUTRALIZER APPLICATION | The first amount of neutralizer (oxidising agent) is applied, using one half the volume as was utilized of the reducing agent. This is left for 5 minutes. The second application, using remaining neutralizer, is applied to the still wound mandrels, and left for 5 minutes |
| RINSING/ CONDITIONING | The mandrels are removed, and an acid conditioning rinse applied. This is massaged through the hair and then rinsed. |
| STYLING | Drying and styling is performed with no cautions issued on special care. Oxidation is complete, and the customer can commence with further chemical treatment, e.g. permanent dyeing, should she desire. |

INDUSTRIAL APPLICABILITY

The process of the invention can be used to reconfigure keratin fibre such as human hair, dog's hair, wool from sheep or goats or keratin fibre on or from other suitable sources.

When the process of the present invention is applied to the permanent waving of human hair there are a number of substantial benefits. A customer in a hairdressing salon does not have to be subjected to a rinsing step after the application of reducing agent but before the application of oxidizing agent and hence the customer does not have to spend 20 minutes or more over a basin. Thus there is no need for a blotting step blotting after the application of reducing agent but before the application of oxidizing agent and hence no damage to the hair is caused from such a blotting step. Colouring can be done immediately before or straight after a permanent wave as colour is not lost nor does the dropping of the perm occur. More flexible perm winding can be performed thus providing a greater variety of styles. There are very direct cost saving factors such as in reduced volume of hot water used, reduced number of towels required and increased stylists' time available to handle a greater number of clients.

What we claim is:

1. A process of reconfiguring keratin fibre consisting essentially of: rolling, winding, curling, looping, lapping, folding, twirling, bending, curving, twisting, coiling, twining, entwining or straightening the keratin fibre or leaving the keratin fibre unchanged; applying to the keratin fibre a first solution to even out the porosity of the fibre and a reducing solution having a pH of between 7.5 and 9.5, said first solution being applied to the fibre prior to or when applying said reducing solution, said reducing solution comprising a reducing agent, carbonic acid and ammonium hydroxide, said reducing solution being applied to the keratin fibre to reduce cystine disulfide linkages and other susceptible linkages in the keratin fibre;

applying an oxidizing solution comprising an oxidizing agent and a second solution to even out the porosity of the keratin fibre to the keratin fibre without rinsing the reducing solution prior to applying the oxidizing solution, said oxidizing solution being effective to set cystine disulfide linkage in the keratin fibre;

removing the reducing solution and the oxidizing solution from the keratin fibre by rinsing the keratin fibre.

2. A process according to claim 1, further comprising: washing said keratin fibre before said keratin fibre is rolled, wound, curled, looped, lapped, folded, twirled, bent, curved, twisted, coiled, twined, entwined or straightened or said keratin fibre is left unchanged, to clean said keratin fibre.

3. A process according to claim 1 wherein each of said first and second solutions comprises an aqueous/alcoholic solution containing 18% of total solution of 1 part vinylpyrrolidone/vinyl acetate copolymers to 2 parts quaternized copolymers of vinylpyrrolidone and k-dimethylaminoethyl methacrylate and 3% amino acids.

4. A process according to claim 1 wherein each of said first and second solutions comprises: 32 wt % alcohol, 6 wt % vinylpyrrolidone/vinyl acetate copolymer, 12 wt % quanternized copolymers of vinylpyrrolidone and k-dimethylaminoethyl methacrylate, 3 wt % amino acids and 47 wt % water.

5. A process according to claim 1, wherein said keratin fibre is selected from the group consisting of human hair, dog hair, wool from sheep and wool from goats.

6. A process according to claim 1, wherein said reducing agent is selected from the group consisting of thioglycolic acid, thioglycolic acid derivatives and non-mercaptan reducing compounds.

7. A process according to claim 1, wherein said reducing agent is left on said keratin fibre for a period of from 5 to 40 minutes before applying said oxidizing agent.

8. A process according to claim 1, wherein said oxidizing agent is selected from the group consisting of sodium bromate, hydrogen peroxide, organic peroxides, inorganic metallic peroxides and air.

9. A process according to claim 1, wherein said oxidizing agent is applied to said keratin fibre having the reducing agent for a period of from 5 to 30 minutes.

10. A process according to claim 1, wherein said reducing agent and said oxidizing agent is applied to said keratin fibre in a ratio 1:0.3 to 1.5:1 wt/wt reducing agent:oxidizing agent.

11. A process according to claim 10, wherein said ratio is 1.2:1 wt/wt reducing agent:oxidizing agent.

12. A process according to claim 1, further comprising: applying an acid conditioning rinse to said keratin fibre immediately before the reducing and oxidizing agent are removed.

13. A process according to claim 1, further comprising: applying an acid conditioning rinse to said keratin fibre after removing said oxidizing and reducing agents and then removing said conditioning rinse from said keratin fibre by rinsing said keratin fibre.

14. A process according to claim 1, further comprising: chemically treating said keratin fibre substantially immediately after removing said reducing and oxidizing agents.

15. A process according to claim 14, wherein said chemically treating is selected from the group consisting of:

permanent dyeing, temporary dyeing, highlighting, bleaching, streaking and conditioning.

* * * * *